US009750921B2

(12) United States Patent
Myla

(10) Patent No.: US 9,750,921 B2
(45) Date of Patent: Sep. 5, 2017

(54) VALVE PLANE LOCATOR METHOD AND DEVICE

(71) Applicant: Subbarao V. Myla, Newport Coast, CA (US)

(72) Inventor: Subbarao V. Myla, Newport Coast, CA (US)

(*) Notice: Subject to any disclaimer, the term of this patent is extended or adjusted under 35 U.S.C. 154(b) by 126 days.

(21) Appl. No.: 14/260,167

(22) Filed: Apr. 23, 2014

(65) Prior Publication Data

US 2014/0350388 A1    Nov. 27, 2014

Related U.S. Application Data

(60) Provisional application No. 61/815,189, filed on Apr. 23, 2013.

(51) Int. Cl.
| | | |
|---|---|---|
| *A61M 25/00* | (2006.01) | |
| *A61M 25/01* | (2006.01) | |
| *A61M 25/04* | (2006.01) | |
| A61M 25/06 | (2006.01) | |
| A61B 6/00 | (2006.01) | |

(52) U.S. Cl.
CPC ........ *A61M 25/0108* (2013.01); *A61M 25/04* (2013.01); *A61B 6/487* (2013.01); *A61M 2025/0096* (2013.01); *A61M 2025/0175* (2013.01); *A61M 2025/0681* (2013.01)

(58) Field of Classification Search
CPC .......................... G06T 2207/30101; A61B 6/12
USPC ........................................................ 600/424
See application file for complete search history.

(56) References Cited

U.S. PATENT DOCUMENTS

| | | | | |
|---|---|---|---|---|
| 5,769,821 A | * | 6/1998 | Abrahamson | A61M 25/04 604/104 |
| 6,196,996 B1 | * | 3/2001 | Teirstein | A61M 25/1002 600/3 |
| 7,004,176 B2 | | 2/2006 | Lau | |
| 2004/0138570 A1 | * | 7/2004 | Nita | A61B 17/22012 600/466 |
| 2004/0204737 A1 | * | 10/2004 | Boismier | A61F 2/013 606/200 |
| 2005/0004597 A1 | * | 1/2005 | McGuckin | A61F 2/013 606/200 |
| 2005/0245892 A1 | * | 11/2005 | Elkins | A61M 25/0043 604/508 |
| 2008/0009746 A1 | | 1/2008 | Forster et al. | |
| 2008/0071361 A1 | * | 3/2008 | Tuval | A61F 2/2418 623/2.1 |

(Continued)

OTHER PUBLICATIONS

Achenbach, S. et al., "Determination of the Aortic Annulus Plane in CT Imaging—A Step-by-Step Approach," *JACC: Cardiovascular Imaging*, vol. 6, No. 2, Feb. 2013, pp. 275-280, 4 pages.

(Continued)

*Primary Examiner* — Tse Chen
*Assistant Examiner* — Joanne Hoffman
(74) *Attorney, Agent, or Firm* — Inskeep IP Group, Inc.

(57) ABSTRACT

A catheter system is disclosed, having a plurality of expandable arms with radiopaque markers at their ends. Once deployed at a patient's valve, a user can obtain a correct 3D localization image for placement of the replacement valve by aligning the radiopaque markers to be substantially equidistant from each other and substantially located in the same plane, relative to the sensor of an X-Ray machine.

12 Claims, 6 Drawing Sheets

(56) References Cited

U.S. PATENT DOCUMENTS

| | | | |
|---|---|---|---|
| 2009/0118760 A1* | 5/2009 | Clausen | A61B 17/221 606/200 |
| 2009/0319037 A1* | 12/2009 | Rowe | A61F 2/2418 623/2.11 |
| 2010/0286657 A1* | 11/2010 | Heck | A61M 25/0023 604/508 |
| 2011/0052026 A1 | 3/2011 | Liao et al. | |
| 2011/0249794 A1 | 10/2011 | Florent et al. | |
| 2012/0207365 A1 | 8/2012 | Verstraeten et al. | |
| 2012/0323545 A1 | 12/2012 | Aulbach et al. | |

OTHER PUBLICATIONS

Kasel, A.M. et al., "Fluoroscopy-Guided aortic Root Imaging for TAVR,"*JACC: Cardiovascular Imaging*, vol. 2, No. 2, Feb. 2013, pp. 274-275, 2 pages.

* cited by examiner

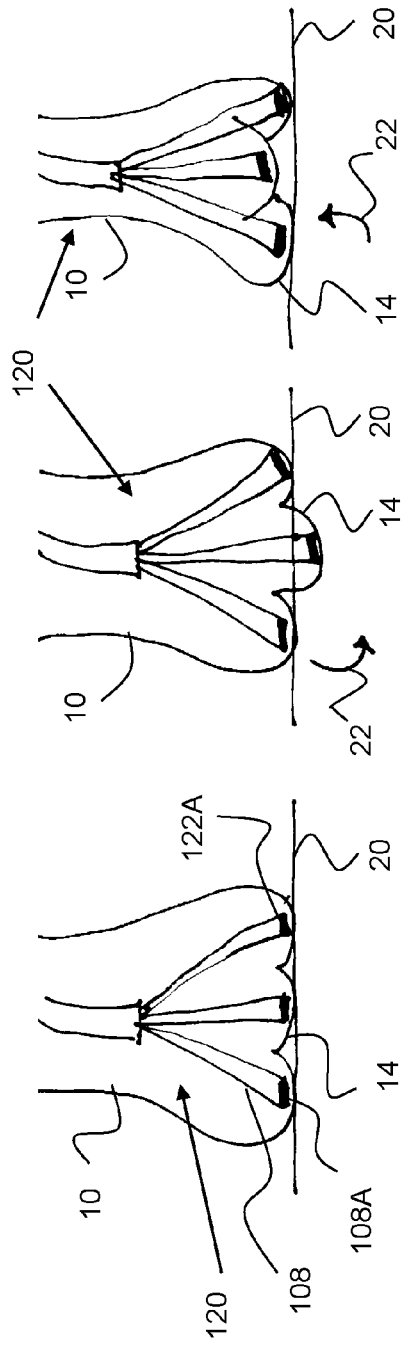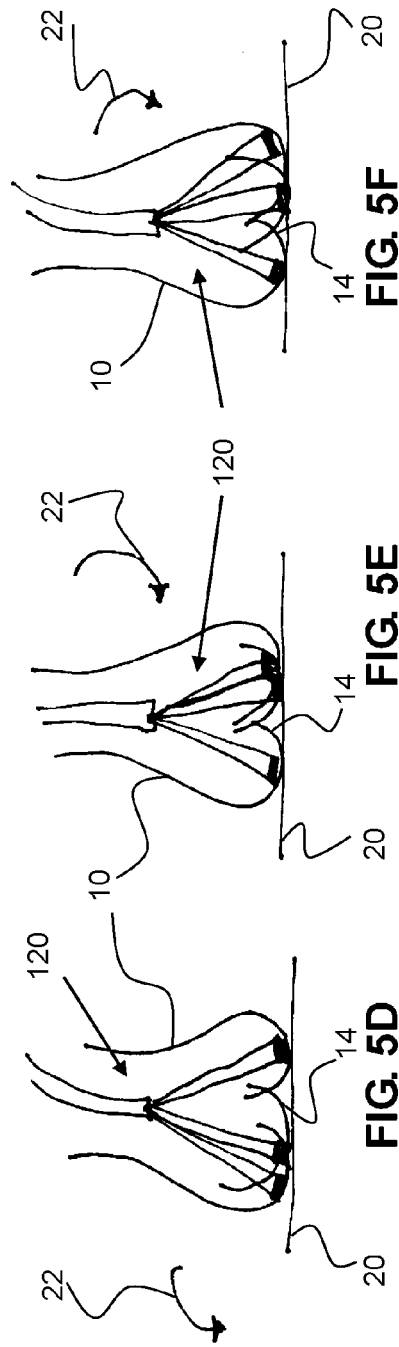

VALVE PLANE LOCATOR METHOD AND DEVICE

RELATED APPLICATIONS

This application claims priority to U.S. Provisional Application Ser. No. 61/815,189 filed Apr. 23, 2013 entitled Valve Plane Locator Method And Device, which is hereby incorporated herein by reference in its entirety.

FIELD OF THE INVENTION

The present invention relates to methods and devices for locating the plane of body organ and more particularly to locating the plane of a heart valve of a patient to facilitate the safe effective deployment of a replacement heart valve in that patient.

BACKGROUND OF THE INVENTION

In the emerging field of catheter based valve interventions without open heart surgery, localization of the valve plane is important for deployment of artificial heart valves. Inaccurate localization leads to misplacement of the valve and thus potentially causes serious complications such as valve dislodgement, leakage due to lack of an effective seal and obstruction of adjacent vital structures such as coronary arteries. Such complications obviously are not safe for the patient and very often threaten the patient's life.

Current methods of valve plane localization include the use of fluoroscopy whereby the interventionalist obtains fluoroscopic images of the valve region until the optimal orthogonal projections of the valve root are obtained. These projections are then used as frame of reference for proper placement of the replacement valve. An article that describes one such fluoroscopic approach to valve placement is *Fluoroscopy-Guided Aortic Root Imaging* for TAVR as found in the "Letters to the Editor" section of the JACC: Cardiovascular Imaging, Vol. 6, No. 2, 2013, the entire contents of which is incorporated herein by reference.

Another method of valve plane localization is the use of Computed Tomography (CT) Imaging. The CT images from a patient's valve root are manipulated using software to enable the interventionalist to locate the valve plane and thus use those images for proper placement of the replacement valve. An article that describes one such CT Imaging approach to valve placement is *Determination of the Aortic Annulus Plane in CT Imaging—A Step by step Approach*, J Am Coll Cardiol Img. 2013; 6(2):275-278, dated Jun. 15, 2012, the entire contents of which is incorporated herein by reference.

There are non-trivial drawbacks, however, to current approaches to valve plane localization. For example, fluoroscopy approaches tend to require the use of significant amounts of contrast medium which, in turn, places a significant burden on the patient's kidneys. Another example is that CT imaging requires the use of a cumbersome and very expensive imager. Hence, there are significant barriers to gaining wide acceptance of CT imaging as a placement tool.

As a result there is a strong need for a device and method that effectively achieves valve plane localization and that is safer for the patient and more readily available to a wide spectrum of interventionalists.

OBJECTS AND SUMMARY OF THE INVENTION

It is an object of the present invention to provide a catheter device that enables a user to easily and accurately localize the valve plane of valve in a patient's heart.

It is a further object to provide a method that enables a user to easily and accurately localize the valve plane of a valve in a patient's heart.

It is a further object to provide a device and method that can be widely and effectively used in the safe deployment of implants and particularly replacement heart valves.

In one embodiment, a catheter system is disclosed, having a plurality of expandable arms with radiopaque markers at their ends. Once deployed at a patient's valve, a user can obtain a correct 3D localization image for placement of the replacement valve by aligning the radiopaque markers to be substantially equidistant from each other and substantially located in the same plane, relative to the sensor of an X-Ray machine.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 5A-5F are cross-sectional views of the valve plane of an aortic valve of a patient showing deployment of a catheter in accordance with the present invention and further showing images of possible placement of the catheter deployment along with a direction the X-Ray imager should be adjusted in order for accurate visualization of the catheter in its deployed state;

DESCRIPTION OF EMBODIMENTS

Figure 1:
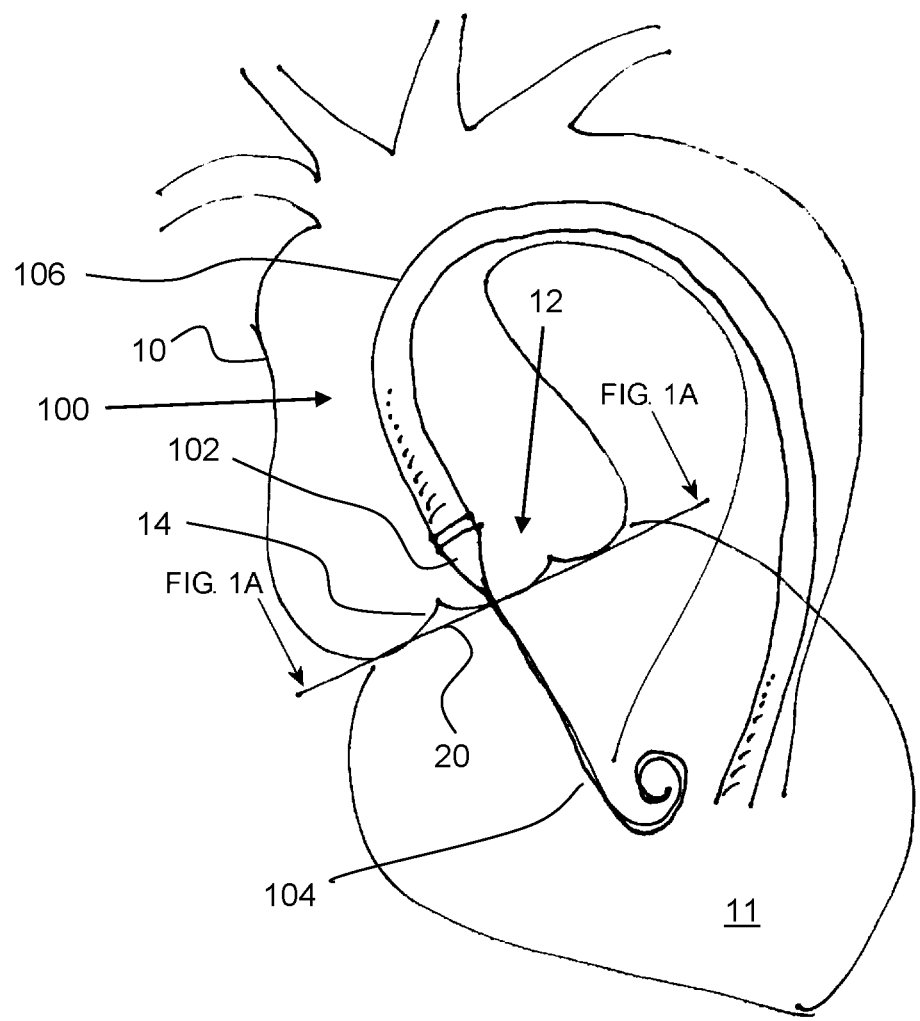
FIG. 1 is a cross-sectional view of the aortic root region of a patient's heart showing an initial placement of a catheter in accordance with present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Referring to FIG. 1, a catheter system 100 for localizing a valve plane in accordance with a preferred embodiment if the present invention is shown inserted in a patient with the distal end of the catheter 100 located at the aortic valve 12 of the patient. The catheter 100 has been delivered over a guide wire 104 to the aortic valve 12, the pig tail of which is located in the left ventricle 11 of the patient's heart.

Figure 1A:
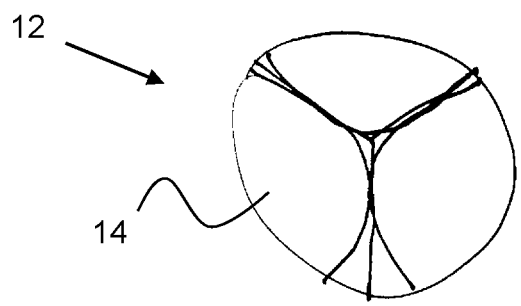
FIG. 1A is a top planar view of the aortic valve plane of FIG. 1.

Referring to FIG. 1A, the distal tip of the catheter system 100 or stylet 102 is located primarily in the center of the valve where the three cusps of the aortic valve leaflets 14 meet. The distal tip of the catheter or the stylet 102 is pointed or cone-shaped so as to more easily center the catheter between all three cusps.

Figure 2:
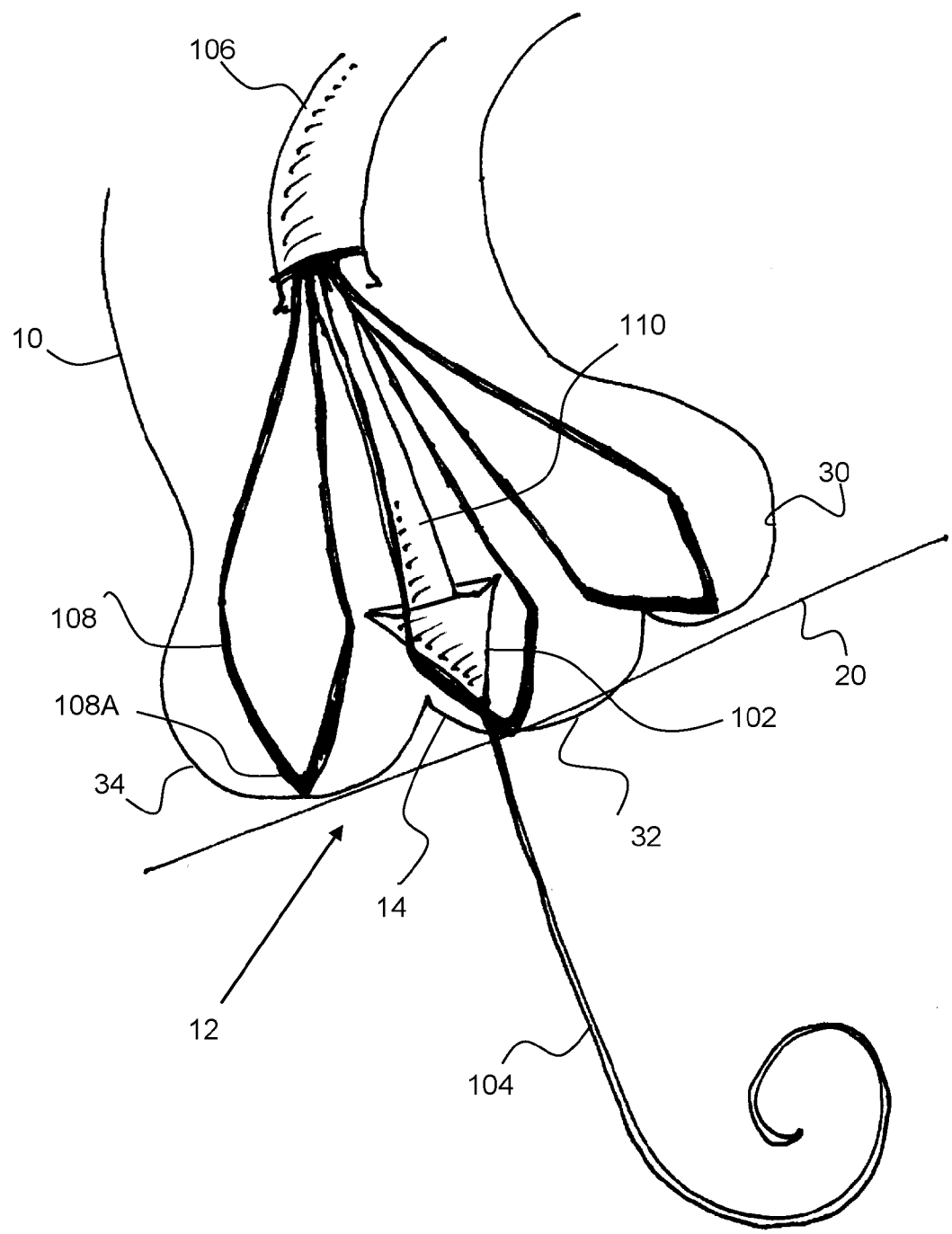
FIG. 2 is a cross-sectional view of the aortic root region of a patient's heart showing deployment of a catheter in accordance with the present invention.

Referring to FIG. 2, an outer catheter/sheath device 106 has been withdrawn from the distal stylet 102 of the catheter 100, thus exposing an inner catheter 110 and deploying three aortic valve plane petals 108. In this embodiment, each of the petals 108 are formed from a wire, angled to a generally diamond or trapezoid shape. Preferably, the petals 108 are configured (e.g., via shape-memory material such as Nitinol) to radially, outwardly expand when unconstrained to positions that are equidistant from each other or adjacent petals 108. The tip of each petal 108 includes a radiopaque material or coating so that the tip of each petal 108 is easily visible during fluoroscopy.

When deployed, the tip of each valve plane petal 108 expands to or becomes located in one of the left coronary cusp (30), the right coronary cusp (32) and the non-coronary cusp (34), respectively. As will be described below, when each of the tips 108A of the valve plane petals 108 are viewed to be located substantially equidistant from each other and substantially all on one plane, namely, the aortic valve plane 20, the user then has a frame of reference from which a replacement valve can be properly deployed in the aortic root.

Figure 3:
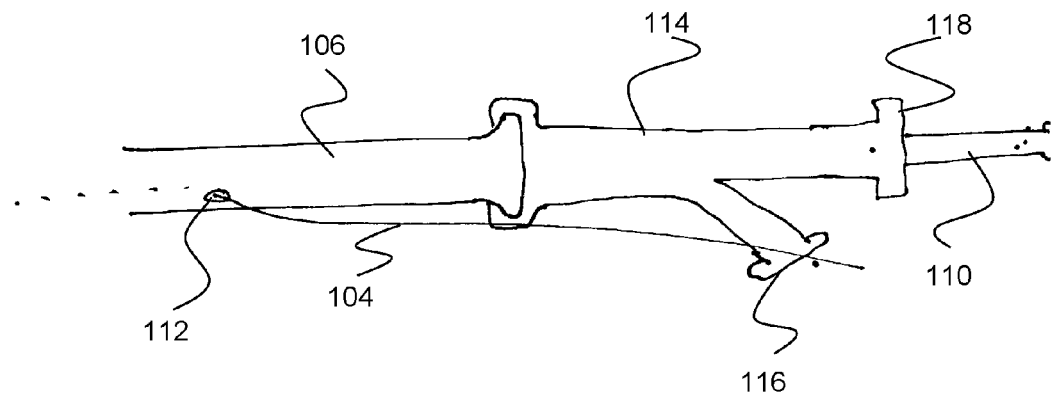
FIG. 3 is a partial view of a back-end region of a catheter system in accordance with the present invention.

Referring to FIG. 3, the back end of the catheter device 100 includes an outer guide catheter 106 having an example size of 6-8 F. A guide wire opening 112 is located on the outer guide catheter 106. Attached to the proximal end of the outer guide catheter 106 is a Touhe-Borst Y connector 114 with a flush port 116. The inner catheter 110 containing the valve plane petals 108 is insertable through the proximal end or hub 118 of the Y Connector 114 and into the outer guide catheter 106. In a preferred embodiment the inner catheter 110 has a guidewire access port 110A (FIG. 4) so that the inner catheter 110 can be guided to the valve root over a guide wire 104. Placement of the catheter system 100 can made through several different vascular routes.

Figure 4:
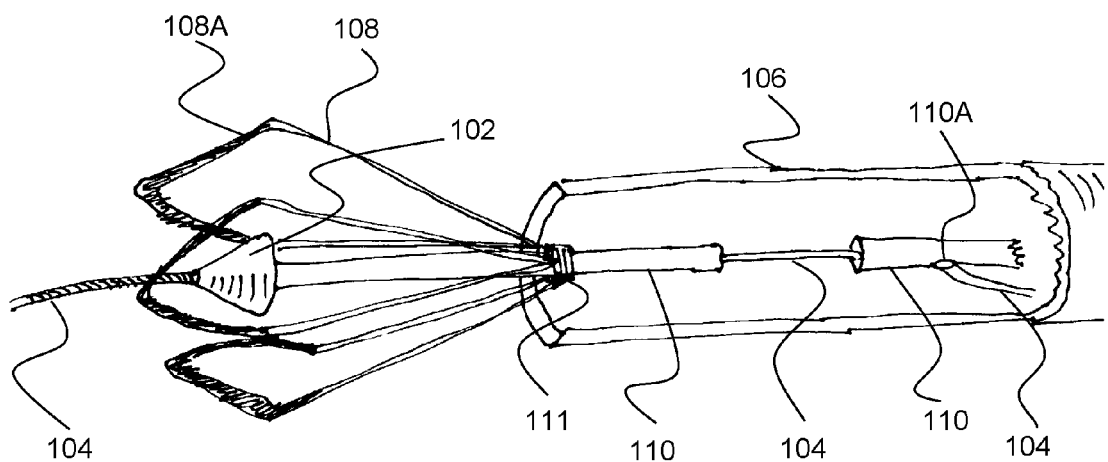
FIG. 4 is a partial cross-sectional view of a working end of a catheter system in accordance with the present invention.
Figure 6A:
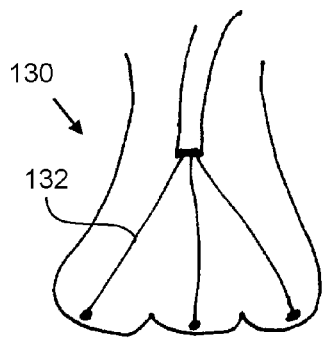
FIGS. 6A-6F show cross-sectional views in the aortic root of a patient's aortic valve of other preferred embodiments of a catheter in accordance with the present invention; and, FIG. 7 illustrates a side view of a catheter system in accordance with the present invention.
Figure 6B:
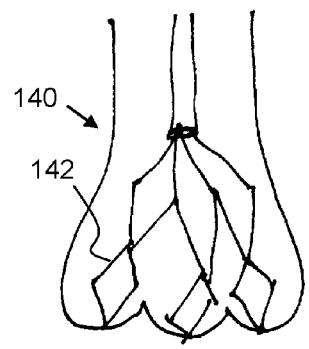
Figure 6C:
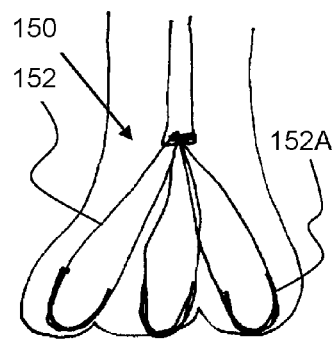
Figure 6D:
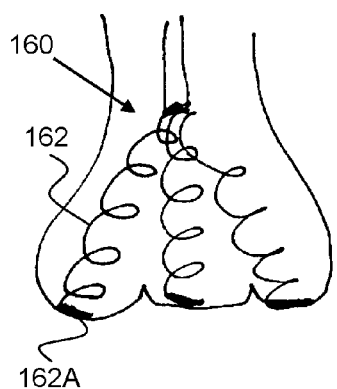
Figure 6E:
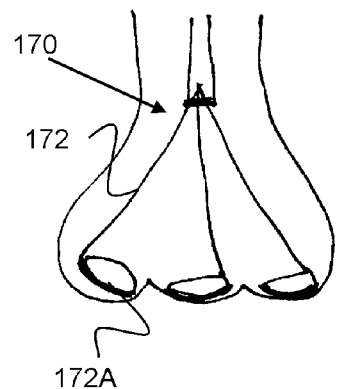
Figure 6F:
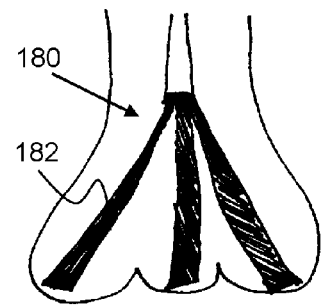

Referring to FIG. 4, the working end, or distal end, of the inner catheter 110 includes a bumper 111 to which the valve plane petals 108 are connected. Prior to withdrawing the outer catheter, the petals are constrained over the inner catheter 110 by the outer catheter/sheath 106. In other words, the petals 108 are biased to expand outwardly in three dimensions and are held against that bias by the outer catheter/sheath 106. In a preferred embodiment, the guide wire 104 is a 0.035 inch guidewire and extends through the inner catheter 110 and out through the stylet 104 of the catether 110. The system is designed so that the catheter 110 and petals 108 are repositionable and retractable into the outer catheter/sheath for introduction and removal from the vasculature of the patient.

As will be appreciated to one of skill in the art, the catheter system design allows for wide approximation of the outer diameter of the valve plane 20. It also avoids interference with the blood flow across the valve 12.

The valve plane petals 108 are self-expanding wire frame designs that are retractable into the coaxial delivery catheter/sheath 106. In a preferred embodiment, the wire frame diameters for the petals 108 can range from 0.014" to 0.035". The tips 108A are configured to have radiopacity that is easily detectable using X-Ray fluoroscopy.

In a preferred embodiment, the outer catheter 106 is made of standard catheter materials such as Teflon and wire braided to provide support and kink-resistance. A coaxial design ensures proper incorporation of the inner catheter 110 with its valve plane petals 108. The Catheter system can be further configured for use via monorail and over-the-wire platforms to provide diversity of usage. In a preferred embodiment, the diameters of the catheters range from 5-10 F. In a preferred embodiment, the distal end of the outer catheter 106 has a radiopaque marker band.

Referring to FIGS. 5A-5F, depending on the orientation of the gantry of the X-Ray machine in the catheter lab relative to the patient's heart, the location of the radio opaque tips 108A of the petals 108 in their respective valve cusps will appear differently on the X-ray images. FIGS. 5A-5F are representative of the appearance of those images.

The objective of the interventionalist is to orient the gantry of the X-Ray machine so that the image obtained from the X-Ray fluoroscopy shows the tips 108A of the valve plane petals 108 to be (1) all substantially equidistant from each other; and, (2) all located substantially on the same plane. When this image is obtained, the interventionalist then has an accurate 3D localization of the aortic root and can then properly deploy the replacement valve. In this regard, FIGS. 5A-5F also indicate which direction 22 the gantry should be rotated for a given non-equidistant, non-planar orientation of the valve plane petals.

Referring next to FIGS. 6A-6F, there are shown various alternative preferred embodiments for the structure and configuration of the valve plane petals. In the catheter embodiment 130 of FIG. 6A, the valve plane petals are composed of single wire members 132 which each have a radiopaque marker at their distal end. In the catheter embodiment 140 of FIG. 6B, a plurality of diamond or scissor linkages 142 make up each valve plane petal, with radiopaque regions at their distal ends. The catheter embodiment 150 of FIG. 6C includes a plurality of loop or teardrop-shaped petals 152 that each include a distal radiopaque region 152A. The catheter embodiment 160 of FIG. 6D have valve plane petals 162 each composed of a spiral or helically-shaped wire with a radiopaque distal end 162A. The catheter embodiment 170 of FIG. 6E includes valve plane petals 172 formed from a relatively straight wire that forms a distal, radiopaque loop 172A. Finally, the catheter embodiment 180 of FIG. 6F includes valve plane petals 182 having a solid, rectangular shape and including radiopaque material along a portion of its length.

Figure 7:
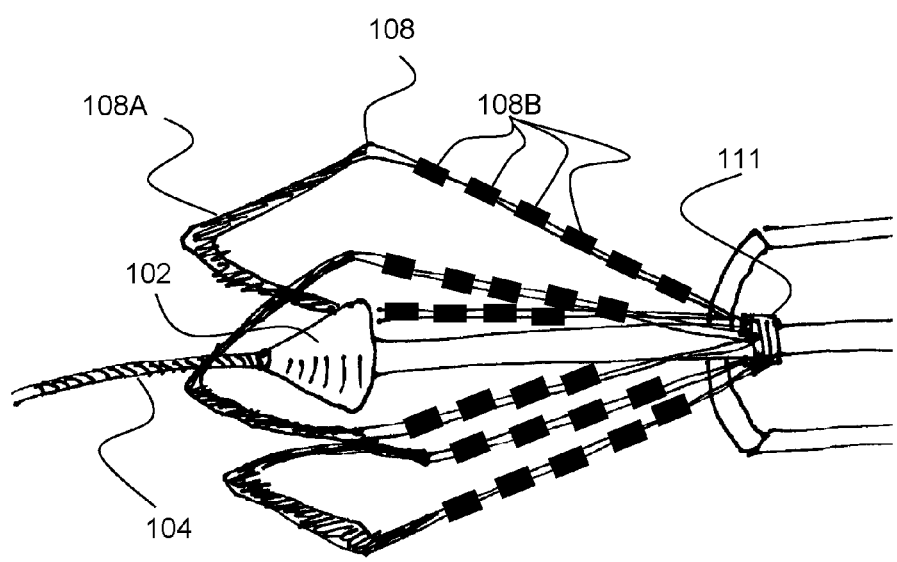

Turning to FIG. 7, another catheter embodiment is shown in which the valve plane petals 108 include a plurality of regularly spaced radiopaque markers 108B between its distal end and the bumper 111. Preferably, these markers 108B are spaced at the same distance from each other, however, the spacing can also increase or decrease in size between the distal end and bumper 111. These markers 108B can be used to as reference or measuring points so as to more accurately determine or calibrate the dimensions and/or geometry of the aorta.

A preferred embodiment of the present invention as it relates to aortic valve replacement includes accessing the aortic root of the patient through traditional means. A guide wire 104 is then inserted into the vasculature and is routed through the aorta 10, through the aortic valve 12 so that a distal end of the guide wire 104 is located in the left ventricle 11 of the patient's heart.

In one embodiment, both the inner catheter 110 and outer catheter 106 can be simultaneously advanced over the guidewire 104. Specifically, the stylet 102 and inner catheter 110 is advanced over the proximal end of the guidewire 104, allowing the guidewire's proximal end to exit out port 110A of the inner catheter 110 and out port 112 of the outer catheter 106, until the stylet 102 and the distal end of the outer catheter 106 are located between all three of the cusps of the aortic valve.

Alternately, the outer catheter 106 can be first advanced over the guidewire 104 until a distal dip of the outer catheter is located near the aortic valve, followed by the inner catheter which is then also inserted over the guidewire.

In either scenario, the distal tip or stylet 102 of the inner catheter 110 is positioned in the center of the valve 12 between all three of the cusps of the aortic valve 12. This can be viewed through traditional fluoroscopic techniques.

The interventionalist then retracts the outer catheter/sheath 106 thus exposing the valve plane petals 108 of the inner catheter 110 and thus allowing the tip 108A of each petal 108 to rest against one of the left coronary 30, right coronary 32, or non-coronary 34 cusps of the aortic valve 12. The user will then observe the positions of the radiopaque tips 108A of the petals via X-Ray fluoroscopy.

Depending on the observed positions of the radiopaque tips 108A of the petals 108, the user will rotate the gantry of the X-Ray machine until the user obtains a view where the radiopaque tips are substantially equidistant from each other and are substantially all on the same plane. When this view is obtained, the user has assurance that they have obtained a correct 3-D localization image for placement of the replacement valve.

The user then withdraws the inner catheter 110 and proceeds with the process of deploying the replacement valve using the 3-D localization obtained with the present invention.

It will be appreciated by one of ordinary skill in the art that the method and device in accordance with the present invention is usable with virtually any system whereby a heart valve is being replaced using percutaneous and/or catheter-based means. It will be further appreciated by one of ordinary skill that the method and device in accordance with the present invention is not restricted to use in aortic replacement valve procedures but can be used in any heart valve replacement and, indeed, in any procedure whereby 3-D localization is desired or required.

While three petals 108 are described in these embodiments, it should be understood that more than three petals could also be used, such as 4-10 petals. Additionally, while the petals 108 have been described to self-expand, an expansion mechanism could also be included to allow the user to control expansion.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A catheter system for placement in a body organ, obtaining an X-Ray image of said body organ, and illustrating a valve plane in said body organ, said catheter system comprising:
    an outer catheter sheath for insertion into the vasculature of a patient;
    an inner catheter positioned in said outer catheter; said inner catheter having a distal stylet forming a distally pointed cone-shape centered relative to said inner catheter and that is sized to center said inner catheter in the center of a valve where three aortic valve cusps meet; and,
    three expandable extensions disposed at and non-removably fixed to a distal region of said inner catheter; said expandable extensions each being discrete loops in radially equidistant positions from each other and each having a distal tip; each of said distal tips radially expanding away from said inner catheter relative to a proximal portion of said discrete loops when said outer catheter sheath is proximately withdrawn, such that a distal tip of each of said expandable extensions locate on one of said three aortic valve cusps;
    wherein said distal tip of each of said plurality of expandable extensions are radiopaque,
    wherein imaging said three expandable extensions within said body organ with an X-Ray machine, such that said three expandable extensions are viewed as equidistant and in the same plane, results in said three expandable extensions illustrating said valve plane.

2. The catheter system of claim 1, wherein said wire loops are diamond shaped.

3. The catheter system of claim 1, wherein said wire loops are teardrop-shaped.

4. The catheter system of claim 1, wherein said wire loops are located at the distal end of an elongated wire.

5. The catheter system of claim 1, wherein said plurality of expandable extensions further comprise three radially equidistant rectangular members.

6. A catheter system for placement in a body organ, obtaining an X-Ray image of said body organ, and illustrating a valve plane in said body organ, said catheter system comprising:
    an outer sheath;
    a catheter having a guidewire passage opening at a distal and proximal end of said catheter for passing a guidewire therethrough;
    a stylet forming a distally pointed cone-shape at a center and distal end of said catheter and shaped to center said catheter in a center of a valve where aortic valve cusps meet; and,
    three expandable extensions disposed at and non-removably fixed to a distal region of said catheter; said plurality of expandable extensions each being discrete loops in radially equidistant positions from each other and each having a distal tip; each of said distal tips sized and positioned to radially expand away from said catheter relative to a proximal portion of said discrete loops and rest on said aortic valve cusps when said outer sheath is withdrawn;
    wherein each of said plurality of expandable extensions have a radiopaque material on each of said distal ends;
    wherein imaging said three expandable extensions within said body organ with an X-Ray machine, such that said three expandable extensions are viewed as equidistant and in the same plane, results in said three expandable extensions illustrating said valve plane.

7. The catheter system of claim 6, wherein said plurality of expandable extensions are composed of a shape-memory material and biased to radially expand from said catheter when unconstrained.

8. The catheter system of claim 6, wherein said expandable extensions have a shape of a loop, spiral, or diamond.

9. The catheter system of claim 8, wherein said catheter has a guidewire passage with a distal and proximal opening.

10. The catheter system of claim 8, further comprising an outer sheath located over said catheter.

11. The catheter system of claim 6, wherein said catheter is configured for over-the-wire, monorail use.

12. A method of using a catheter system for placement in a body organ, obtaining an X-Ray image of said body organ, and illustrating a valve plane in said body organ, said method of using a catheter system comprising advancing a catheter system to a valve, said catheter system comprising:

an outer catheter sheath for insertion into the vasculature of a patient;

an inner catheter positioned in said outer catheter; said inner catheter having a distal stylet forming a distally pointed cone-shape centered relative to said inner catheter and that is sized to center said inner catheter in the center of a valve where three aortic valve cusps meet; and, three expandable extensions disposed at and non-removably fixed to a distal region of said inner catheter; said expandable extensions each being discrete loops in radially equidistant positions from each other and each having a distal tip; each of said distal tips radially expanding away from said inner catheter relative to a proximal portion of said discrete loops when said outer catheter sheath is proximately withdrawn, such that a distal tip of each of said expandable extensions locate on one of said three aortic valve cusps;

wherein said distal tip of each of said plurality of expandable extensions are radiopaque;

imaging said three expandable extensions within said body organ with an X-Ray machine, such that said three expandable extensions are viewed as equidistant and in the same plane, results in said three expandable extensions illustrating said valve plane.

* * * * *